US007905879B2

(12) United States Patent
Abboud et al.

(10) Patent No.: US 7,905,879 B2
(45) Date of Patent: *Mar. 15, 2011

(54) CRYOABLATION CATHETER HANDLE

(75) Inventors: Marwan Abboud, Pierrefonds (CA);
Domenic Santoianni, Kirkland (CA);
Philippe Marchand, Hudson (CA)

(73) Assignee: Medtronic Cryocath LP, Toronto, Ontario (CA)

( * ) Notice: Subject to any disclaimer, the term of this patent is extended or adjusted under 35 U.S.C. 154(b) by 1083 days.

This patent is subject to a terminal disclaimer.

(21) Appl. No.: 11/499,213

(22) Filed: Aug. 4, 2006

(65) Prior Publication Data

US 2006/0271029 A1 Nov. 30, 2006

Related U.S. Application Data

(63) Continuation of application No. 10/706,525, filed on Nov. 12, 2003, now Pat. No. 7,118,565, which is a continuation of application No. 10/202,991, filed on Jul. 25, 2002, now Pat. No. 6,746,445, which is a continuation of application No. 09/556,042, filed on Apr. 21, 2000, now Pat. No. 6,440,126.

(60) Provisional application No. 60/130,538, filed on Apr. 21, 1999.

(51) Int. Cl.
*A61B 18/02* (2006.01)
(52) U.S. Cl. ............................................. 606/22; 606/21
(58) Field of Classification Search .............. 606/20–26
See application file for complete search history.

(56) References Cited

U.S. PATENT DOCUMENTS

| 3,980,112 | A |   | 9/1976  | Basham            |
|-----------|---|---|---------|-------------------|
| 4,043,341 | A |   | 8/1977  | Tromovitch        |
| 4,534,339 | A |   | 8/1985  | Collins et al.    |
| 4,617,012 | A |   | 10/1986 | Vaillancourt      |
| 4,838,269 | A |   | 6/1989  | Robinson et al.   |
| 4,919,112 | A |   | 4/1990  | Siegmund          |
| 4,946,440 | A |   | 8/1990  | Hall              |
| 5,078,713 | A |   | 1/1992  | Varney            |
| 5,098,428 | A |   | 3/1992  | Sandin et al.     |
| 5,170,787 | A |   | 12/1992 | Lindegren         |
| 5,217,482 | A |   | 6/1993  | Keith             |
| 5,239,982 | A |   | 8/1993  | Trauthen          |
| 5,243,807 | A |   | 9/1993  | Randlett          |
| 5,281,213 | A | * | 1/1994  | Milder et al. ............. 606/15 |
| 5,324,286 | A |   | 6/1994  | Fowle             |
| 5,334,181 | A |   | 8/1994  | Rubinsky et al.   |
| 5,344,398 | A | * | 9/1994  | Hara ..................... 604/97.01 |
| 5,348,554 | A |   | 9/1994  | Imran et al.      |
| 5,395,348 | A |   | 3/1995  | Ryan              |
| 5,437,673 | A |   | 8/1995  | Baust et al.      |
| 5,452,582 | A |   | 9/1995  | Longsworth        |

(Continued)

*Primary Examiner* — Michael Peffley
(74) *Attorney, Agent, or Firm* — Christopher & Weisberg, P.A.

(57) ABSTRACT

A cryocatheter system includes a first handle portion having a proximal end, a distal end, a first fluid flow path, and a second fluid flow path; a second handle portion having a proximal end, a distal end, a first fluid flow path, and a second fluid flow path; and a catheter having a proximal end, a distal end, a first fluid flow path, and a second fluid flow path. The distal end of the first handle portion is matable with the proximal end of the second handle portion to place the respective first and second fluid flow paths of each handle portion in fluid communication; and the distal end of the second handle portion is matable with the proximal end of the catheter to place the respective first and second fluid flow paths of the second handle portion and the catheter in fluid communication.

15 Claims, 6 Drawing Sheets

U.S. PATENT DOCUMENTS

| | | | |
|---|---|---|---|
| 5,466,020 A | 11/1995 | Page et al. | |
| 5,658,278 A | 8/1997 | Imran et al. | |
| 5,674,218 A | 10/1997 | Rubinsky et al. | |
| 5,685,878 A | 11/1997 | Falwell et al. | |
| 5,697,927 A | 12/1997 | Imran et al. | |
| 5,715,817 A | 2/1998 | Stevens-Wright et al. | |
| 5,733,319 A * | 3/1998 | Neilson et al. | 607/105 |
| 5,755,663 A * | 5/1998 | Larsen et al. | 600/374 |
| 5,846,235 A * | 12/1998 | Pasricha et al. | 606/23 |
| 5,860,953 A | 1/1999 | Snoke et al. | |
| 5,860,970 A | 1/1999 | Goddard et al. | |
| 5,916,212 A | 6/1999 | Baust et al. | |
| 5,992,158 A * | 11/1999 | Goddard et al. | 62/51.2 |
| 6,007,571 A | 12/1999 | Neilson et al. | |
| 6,193,644 B1 | 2/2001 | Dobak, III et al. | |
| 6,221,070 B1 | 4/2001 | Tu et al. | |
| 6,224,624 B1 | 5/2001 | Lasheras et al. | |
| 6,241,722 B1 | 6/2001 | Dobak et al. | |
| 6,283,959 B1 * | 9/2001 | Lalonde et al. | 606/21 |
| 6,383,180 B1 * | 5/2002 | Lalonde et al. | 606/22 |
| 6,471,694 B1 * | 10/2002 | Kudaravalli et al. | 606/21 |
| 6,497,703 B1 | 12/2002 | Korteling et al. | |
| 6,648,879 B2 | 11/2003 | Joye et al. | |
| 6,746,445 B2 | 6/2004 | Abboud et al. | |
| 6,989,009 B2 | 1/2006 | Lafontaine | |
| 2002/0095133 A1 | 7/2002 | Gillis et al. | |

* cited by examiner

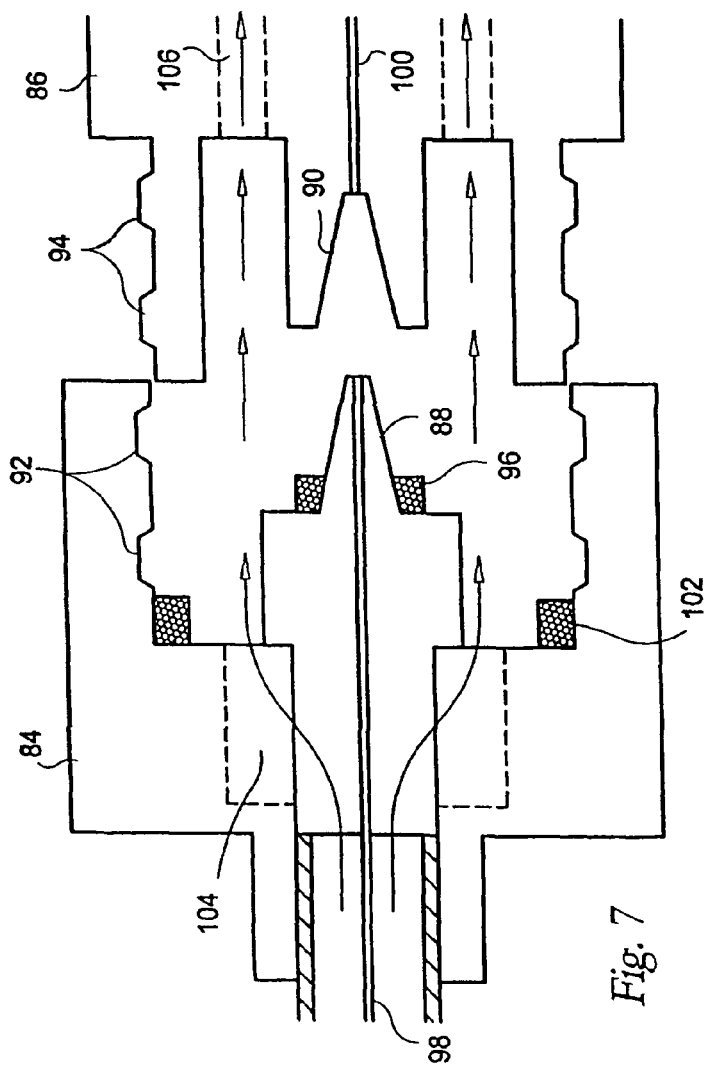
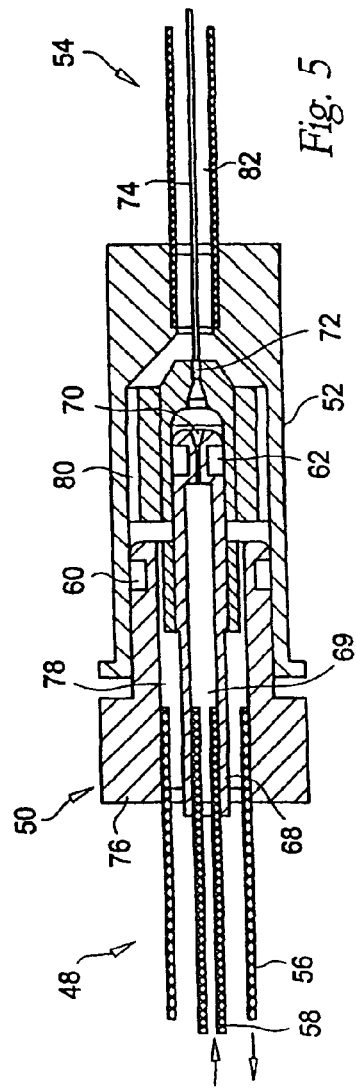
Fig. 7
Fig. 5 of # CRYOABLATION CATHETER HANDLE

CROSS-REFERENCE TO RELATED APPLICATIONS

This application is a Continuation of pending application Ser. No. 10/706,525, filed Nov. 12, 2003, by Marwan Abboud, et al., entitled CRYOABLATION CATHETER HANDLE, now Pat. No. 7,118,565, issued Oct. 10, 2006, which application is a continuation of and claims priority to application Ser. No. 10/202,991, filed Jul. 25, 2002, by Marwan Abboud, et al., entitled CRYOABLATION CATHETER HANDLE, now Pat. No. 6,746,445, issued Jun. 08, 2004, which application is a continuation of and claims priority from U.S. patent application Ser. No. 09/556,042, filed Apr. 21, 2000, by Marwan Abboud, et al., entitled CRYOABLATION CATHETER HANDLE, now Pat. No. 6,440,126, issued Aug. 27, 2002, which application claims priority from U.S. Provisional Patent Application Ser. No. 60/130,538, filed Apr. 21, 1999, by Marwan Abboud, et al., entitled CRYOABLATION CATHETER HANDLE, now lapsed, the totality of all of which are incorporated herein by reference.

STATEMENT REGARDING FEDERALLY SPONSORED RESEARCH

Not applicable.

FIELD OF THE INVENTION

This invention relates to catheters, and more particularly to handles and connectors for cryogenic catheters.

BACKGROUND OF THE INVENTION

A cryocatheter can generally be described as an elongate, slender, flexible body that is capable of delivering extreme cold to provide a medically therapeutic effect. Such a catheter can be a part of a system that includes several components, such as a console, an umbilical, a cryoblation catheter and a handle.

The console houses the electronics and software for controlling an ablation procedure. Additionally, the console controls delivery of a refrigerant through the umbilical to the catheter and recovery of the refrigerant from the catheter.

The umbilical connecting the catheter and handle to the console provides mechanical connections for refrigerant transport and electrical connection for electrical devices and sensors. The handle, in addition to providing an appropriate graspable structure, can include controls for catheter steering, as well as other catheter functions.

Known cryocatheter systems provide a unitary handle and catheter which is intended for a single use. As with other devices, attention to the percentage and content of a system that is disposable (or that which must be disposed of for sanitary reasons), as well as attention to the cost of replacement items, can have a substantial effect on the cost of acquisition and operation of the system. Thus, if possible, it would help to reduce cost of the system if only the catheter (or a portion thereof) were disposable and, under most circumstances, the handle were available for reuse.

Ideally, the inclusion of disposable system elements does not compromise system performance or patient safety. However, known attempts to provide disposable catheter elements have been less than ideal. For example, providing a catheter that is removable from the handle requires not only connection to refrigerant, steering elements and electrical elements, but also a creation of a fluid-tight seal at the catheter/handle interface. Not only can it be tedious to make such connections, known devices with this type of feature have not proved to be acceptable with respect to either performance or safety. It would therefore be desirable to provide a cryocatheter and handle that provides the benefits of a disposable component and which is easy to use, without safety or performance limitations.

SUMMARY OF THE INVENTION

The present invention provides a cyrocatheter system having a two-part handle that is easy to connect and use; but the system does not compromise safety and performance requirements.

In an exemplary embodiment, a cryocatheter system includes a first handle portion having a proximal end, a distal end, a first fluid flow path, and a second fluid flow path; a second handle portion having a proximal end, a distal end, a first fluid flow path, and a second fluid flow path; and a catheter having a proximal end, a distal end, a first fluid flow path, and a second fluid flow path. The distal end of the first handle portion is matable with the proximal end of the second handle portion to place the respective first and second fluid flow paths of each handle portion in fluid communication; and the distal end of the second handle portion is matable with the proximal end of the catheter to place the respective first and second fluid flow paths of the second handle portion and the catheter in fluid communication.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIG. 5 is a sectional view of the two-part co-axial handle of FIG. 4 in a partially mated state;

FIG. 7 is a sectional view of another embodiment of a co-axial connection; and

DETAILED DESCRIPTION OF THE INVENTION

Figure 1:
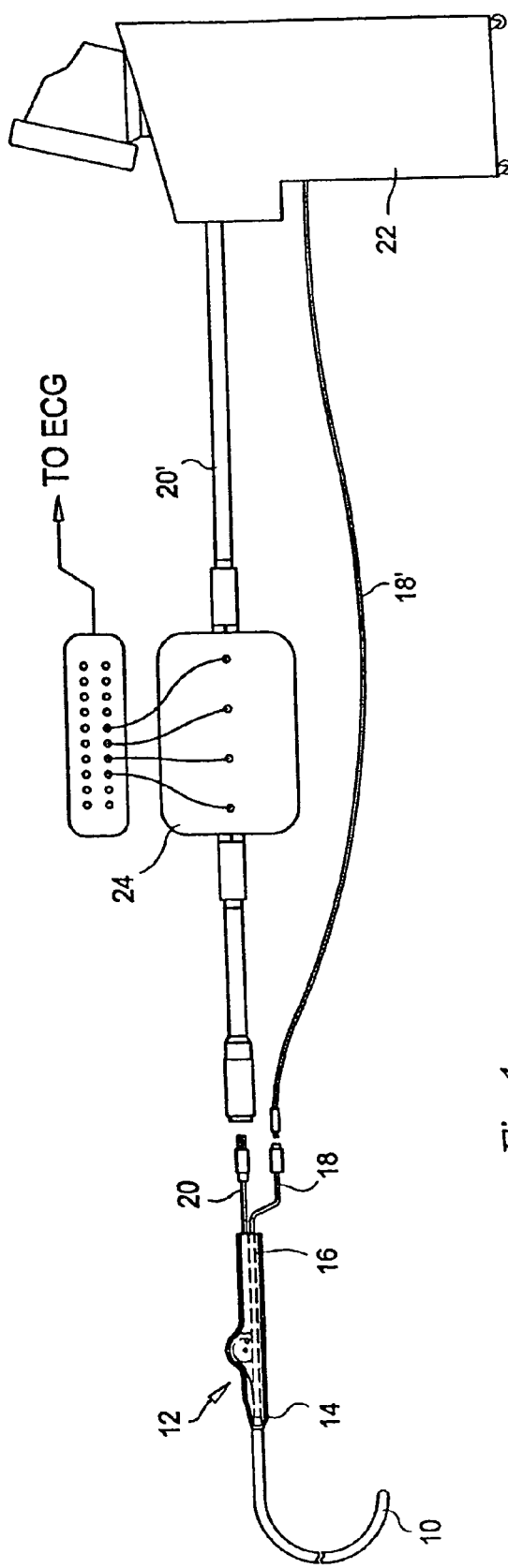
FIG. 1 illustrates a cryocatheter system generally.

FIG. 1 depicts a cryocatheter system in accordance with the invention. The system includes a catheter 10, such as those disclosed in U.S. Pat. Nos. 5,899,898 and 5,899,899 to Arless, which are incorporated herein by reference. The system also includes a handle 12 having a first portion 14 and a second portion 16. First and second umbilicals 18 and 20, respectively, connect the second portion 16 of the handle 12 to a console 22. The first umbilical 18 provides a path for a liquid or gas refrigerant to be transferred between the console 22 and the handle 12; and the second umbilical 20 provides a signal path, such as for electrical signals, between the console 22 and the handle. Additional umbilicals can be provided as required, and the functions of more than one umbilical can be provided in a single, multifunction umbilical. Further, additional devices, such as a connector box 24 can be placed in electrical communication with an umbilical. As shown in FIG. 1, the connector box 24 provides for connection to ECG apparatus (not shown). Also, one or more of the umbilicals can be divisible into two or more portions as shown in FIG. 1, wherein the first umbilical includes portion 18 and 18', and the second umbilical includes portions 20 and 20'.

Figure 2:
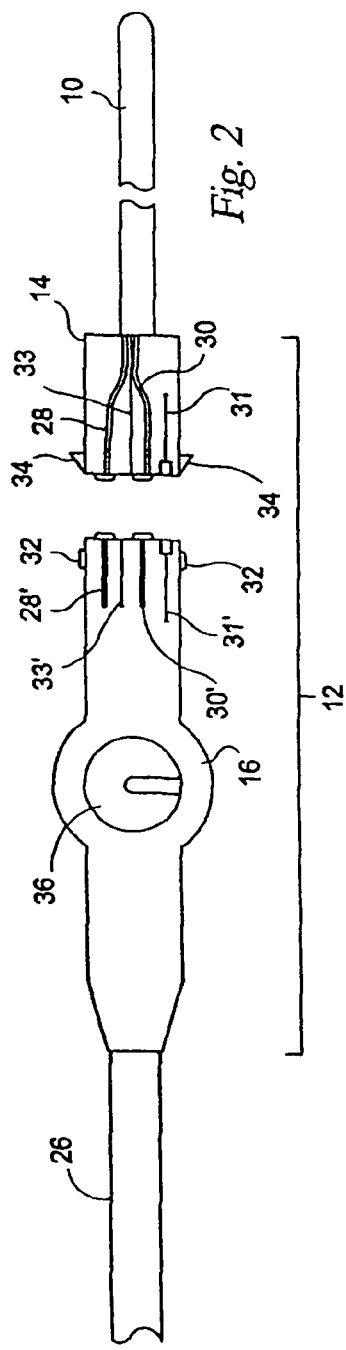
FIG. 2 illustrates an exemplary embodiment of a handle as shown in FIG. 1, wherein the two handle portions are not mated.
Figure 2A:
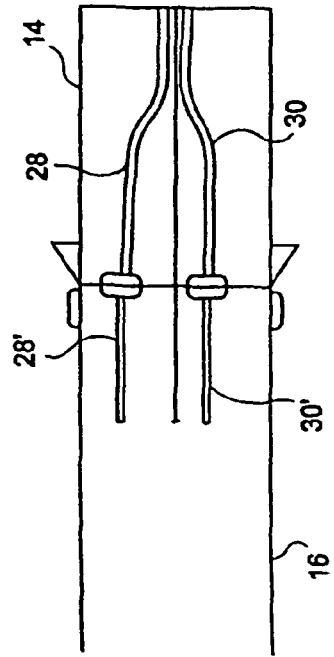
FIG. 2A depicts the first and second handle portions of FIG. 2 in a mated state.

Referring now to FIG. 2, additional details of an exemplary two-part handle 12 are discussed in greater detail. A first handle portion 14 is shown mated to a cryocatheter 10 and a second handle portion 16 is shown mated to a single, multi-purpose umbilical 26. The first handle portion 14 defines or includes a portion of a first fluid pathway 28 and a portion of a second fluid pathway 30. The second handle portion 16 defines or contains a second portion of the first fluid pathway 28' and a second portion of the second fluid pathway 30'. When the first and second portions of the first and second fluid pathways are mated, as shown in FIG. 2A, continuous fluid paths are provided. Similarly, the first handle portion 14 includes a portion of one or more electrical or fiber-optic lines 31 and the second handle portion 16 includes a second portion of the one or more electrical or fiber-optic lines 31'. Further, the first handle portion 14 includes a portion of one or more steering elements, such a pull wire 33 and the second handle portion 16 includes a second portion of the steering elements 33'.

The first and second handle portions, as well as the first and second fluid pathways, one or more electrical or fiber-optic lines, and one or more steering elements are held together by complimentary locking elements 32 and 34 as is known in the art, such as locking clips, bayonet, or twist-lock. Similarly, the fluid paths are mated with couplings, the wires with electrical connectors, and the steering elements with mechanical connectors. Thus, in the exemplary embodiment, the catheter 10 can be disconnected from the umbilical 14 and discarded, while allowing the first handle portion 18, which can include steering mechanisms and other controls, to be retained for further use.

Figure 3:
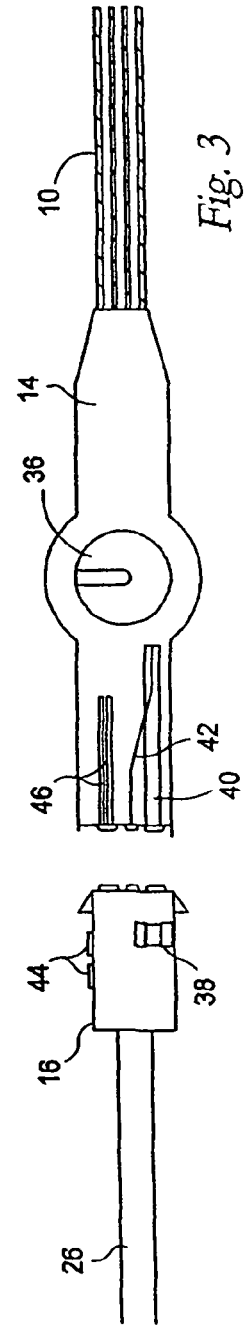
FIG. 3 shows an alternative embodiment of a two-part handle.

Whereas FIG. 2 shows a steering actuator, such as a thumb wheel, for selectively positioning a steering element in the second portion 16 of the handle 12, FIG. 3 shows an arrangement where the steering actuator 36 is located in the first portion 14. Additional features visible in FIG. 3 include a blood sensor 38 located and configured in such a manner so as to detect blood being withdrawn from the catheter 10 through a low pressure or vacuum exhaust line 40 along with refrigerant injected through a supply tube 42. Also shown are electrical controls 44 in communication with electrical wires 46.

Figure 4:
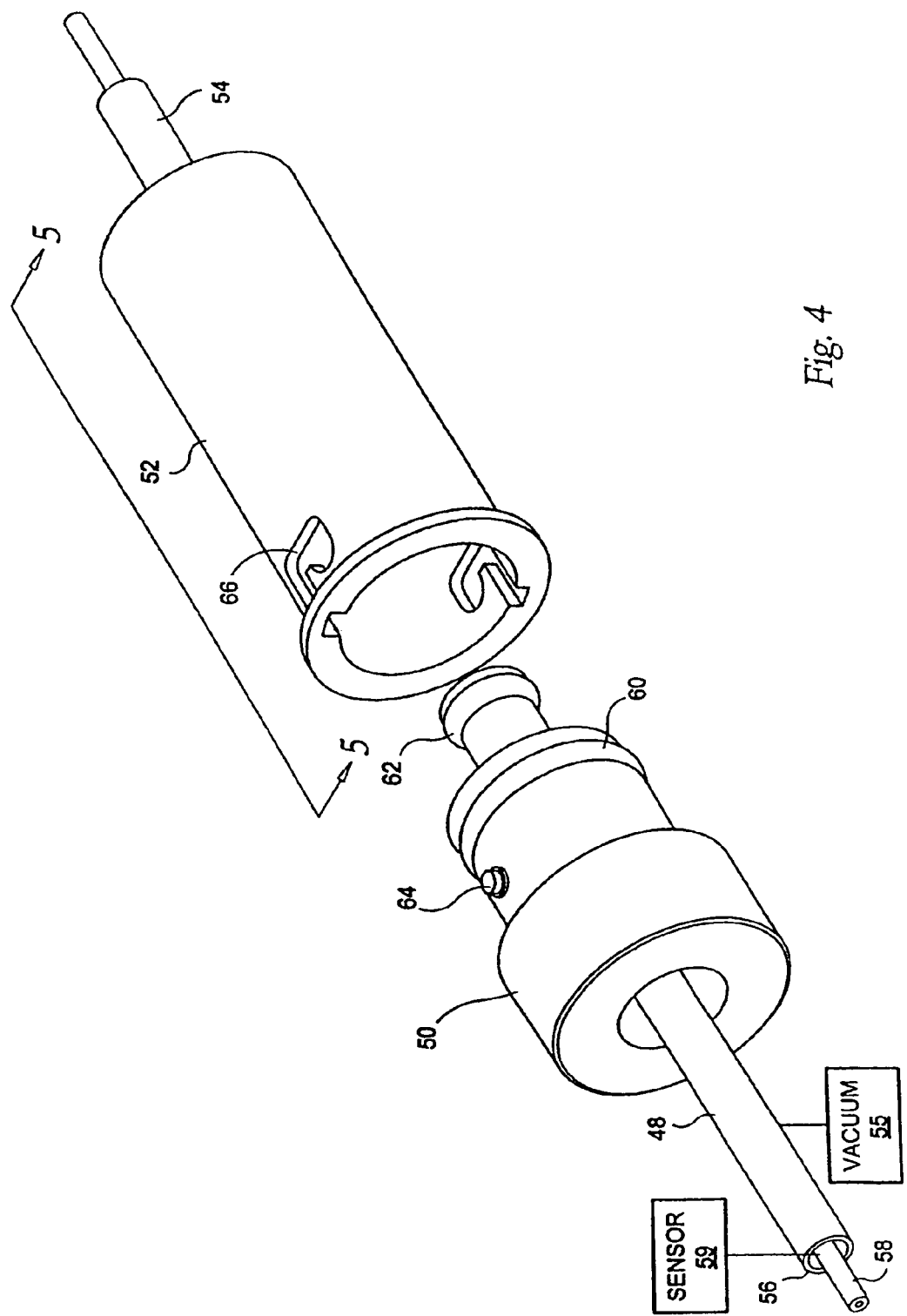
FIG. 4 is an exploded view of a two-part co-axial handle.

In addition to the above features, the refrigerant injection and low pressure or vacuum return lines can be configured coaxially either in an umbilical or in the handle as shown in FIG. 4. In this illustration an umbilical 48, a first connector 50 or handle portion, a second connector 52 or handle portion, and second umbilical 54 or catheter are shown. The umbilical 48 includes an outer tube 56 and an inner tube 58. In the exemplary embodiment, the inner tube 58 provides a path for fluid (e.g., refrigerant) under positive pressure, whereas the outer tube 56 provides a path for fluid under reduced or low pressure (e.g., in connection to a vacuum pump 55). Thus, if a leak should occur at some point along the inner tube 58 or its connections to other components, the low pressure environment allows the leak to be contained, thereby preventing refrigerant from escaping the umbilical 48. Additional safety is provided by a sensor 59 in communication with the low-pressure fluid path defined by the outer tube 56. The sensor 59 is tuned to detect a change in pressure within the outer tube 56, and when a change is detected, fluid flow into the system is turned off, as a change in pressure can be an indicator that a leak is present in the system.

Continuing to refer to FIG. 4, the umbilical 48. is mated to the first connector 50 and the umbilical 54 is mated to the second connector 52. The first connector 50 includes O-rings 60 and 62 and is matable with the second connecter 52, as shown in greater detail in the figures that follow, to provide a fluid-tight connection. The first connector 50 can be locked to the second connector 52 with the assistance of a bayonet-type connection having complimentary protuberances 64 and engagement slots 66.

FIG. 5 is a cross-sectional view of the coaxial connector of FIG. 4 along line 5-5. In this view, the first connector 50 is shown almost fully mated to the second connector 52. In this view the inner tube 58 is shown mated to an inner portion 68 of the first connector 50. The inner portion 68 defines a fluid path 69 leading to an outlet 70 that, when the first and second connectors 50 and 52 are mated, aligns with a fluid inlet 72-to an injection tube 74. The O-ring 62 ensures good sealing of the connection.

Similarly, the outer tube 56 is shown mated to an outer portion 76 of the first connector 50. The outer portion defines a fluid path 78 that is in fluid communication with a fluid path 80 defined by the second connector 52. The fluid path 80 leads to, and is in communication with a fluid path 82 in the umbilical 54. The O-ring 60 ensures a good seal between the first and second connectors 50 and 52, respectively.

Figure 6:
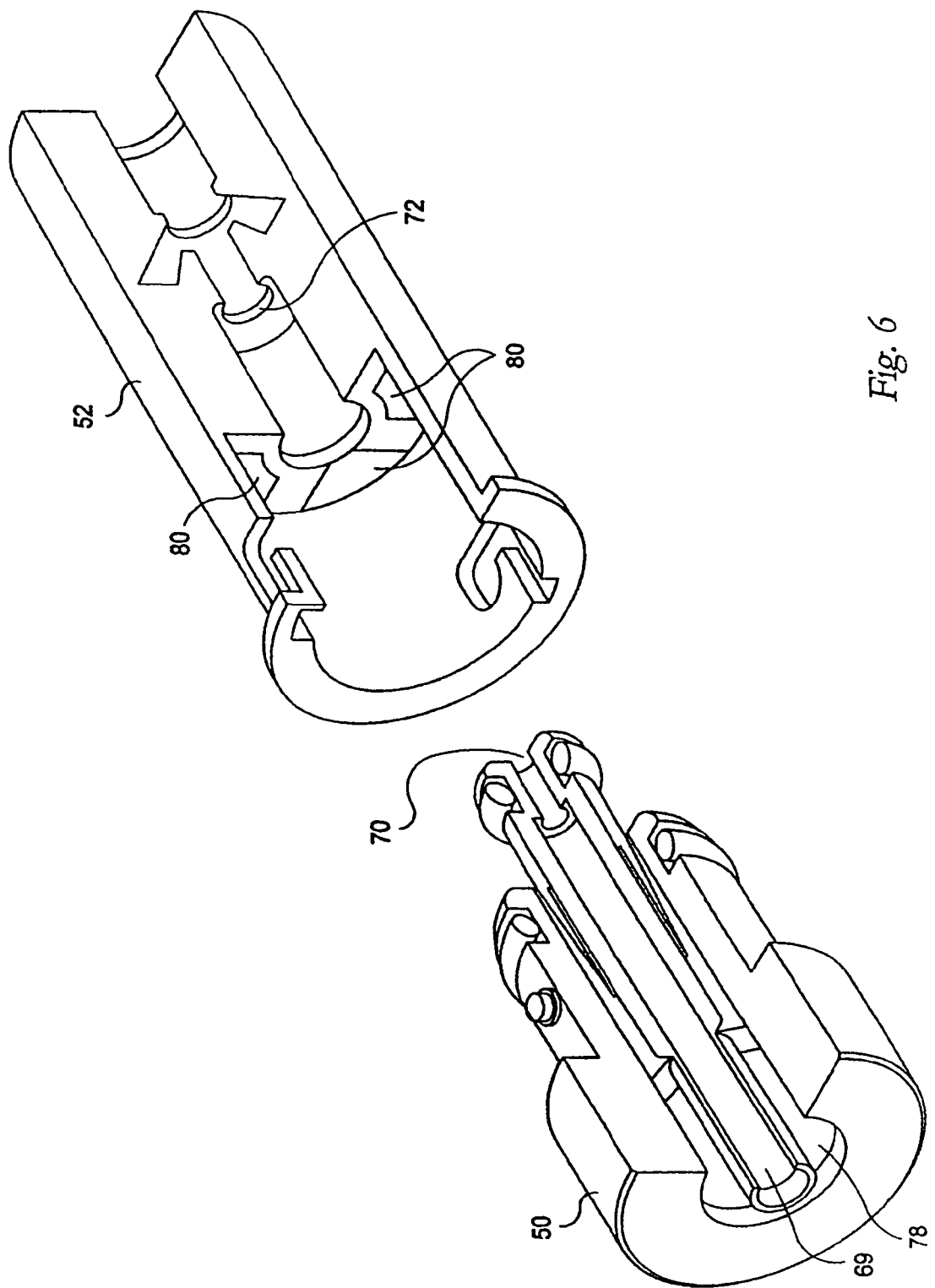
FIG. 6 illustrates additional features of the handle of FIG. 4 in an exploded cut-away view.

FIG. 6 is a cut-away view of the assembly shown in FIG. 6. In this view, the fluid path 69, outlet 70, fluid inlet 72, fluid path 78, fluid path 80 are all clearly visible.

FIG. 7 shows an alternative embodiment of a coaxial arrangement. Shown is a first connector 84 and a second connector 86. In this embodiment, a male Leur taper fitting 88 is receivable within a female Leur taper receptacle 90 as complimentary locking threads 92 and 94 on the first and second connectors are engaged. When the connectors are fully engaged an O-ring seal 96 prevents leakage for connecting fluid flow paths 98 and 100. Similarly, an o-ring seal 102 prevents leakage for connecting fluid flow paths 104 and 106. Exemplary fluid flow through flow paths 104 and 106 is shown by arrows.

Figure 8:
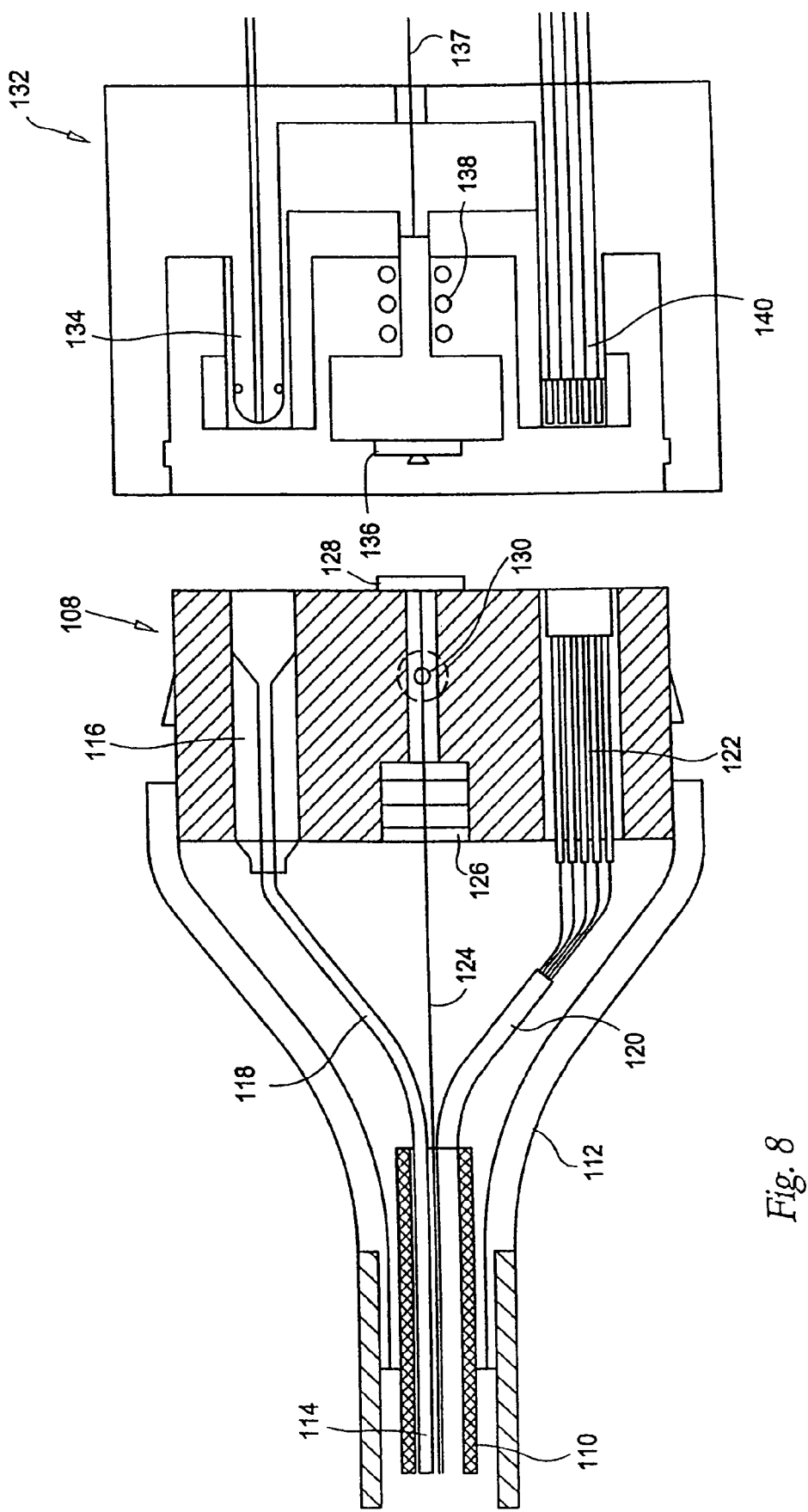
FIG. 8 is yet another embodiment of a co-axial connection.

Yet another connector embodiment is shown in FIG. 8. This embodiment provides connections that are not coaxial. As shown, a first connector 108 is mated to an outer tube or catheter shaft 110 with a rigid sleeve 112 and a flexible strain relief element. An fluid injection tube 114 is connected to a high-pressure female connector fitting 116 with a flexible connector tube 118. Electrical wires 120 that pass through the outer tube 110 terminate at a female pin wire connector 122. A pull-wire 124 passes through the outer tube 110 and a pull-wire seal fitting 126 to a female pull-wire connector 128. A pull-wire tension adjuster 130 can also be provided.

A second connector 132 includes a male, high-pressure connector 134 that is matable with the fitting 116 to provide a continuous fluid path. A male pull-wire connector 136, matable with the connector 128, is axially movable within a portion of the second connector 132 as shown by the double-headed arrow. The connector 136 is secured to a pull-wire 137 that is in turn secured to an actuator (such as element 36 shown in FIGS. 2 and 3). Thus, when the pull-wire 137 is moved axially, the connector 136 moves axially. A bias force can be applied by a bias element 138, such as a spring, to push the connector 136 to a selected point when axial tension is reduced on the pull-wire. Also shown is a male wire pin connector 140.

A variety of modifications and variations of the present invention are possible in light of the above disclosure. It is therefore understood that, within the scope of the appended claims, the present invention may be practiced otherwise than as specifically described hereinabove.

What is claimed is:

1. A catheter system comprising:
a flexible catheter having a proximal end, a distal end, a first fluid flow path, and a second fluid flow path;
a first coupling body having a first electrical connector and defining a first passage and a second passage;
a second coupling body having a second electrical connector and defining a third passage and a fourth passage, the coupling bodies being releasably coupled to each other in a coupled configuration;
such that in the coupled configuration, the electrical connectors are in electrical contact, the first passage and the third passage are in fluid communication with each other and with the first fluid flow path, and the second passage and the fourth passage are in fluid communication with each other and with the second fluid flow path;
a pressure sensor in fluid communication with one of the first and second fluid flow paths;
a source of fluid refrigerant in fluid communication with the first fluid flow path; and
a shutoff element coupled to the pressure sensor and terminating fluid flow through the first fluid flow path upon leak detection.

2. The catheter system of claim 1, wherein the source of fluid refrigerant is pressurized, and the second fluid path is in communication with a vacuum source.

3. The catheter system of claim 1, further comprising a blood sensor in communication with one of the first and second fluid flow paths.

4. The catheter system of claim 3, the blood sensor positioned between the coupling bodies and the distal end.

5. The catheter system of claim 1, further comprising a steering element at least partially disposed within the flexible catheter.

6. The catheter system of claim 5, further comprising a steering actuator coupled to the steering element.

7. The catheter system of claim 1, further comprising a handle coupled to the flexible catheter.

8. The catheter system of claim 1, the pressure sensor positioned between the coupling bodies and the distal end.

9. A catheter system comprising:
a flexible catheter having a proximal end, a distal end, a high-pressure fluid flow path, and a low-pressure fluid flow path;
a first coupling body having a first electrical connector and defining a first passage and a second passage;
a second coupling body having a second electrical connector and defining a third passage and a fourth passage, the coupling bodies being releasably coupled to each other in a coupled configuration;
such that in the coupled configuration, the electrical connectors are in electrical contact, the first passage and the third passage are in fluid communication with each other and with the high-pressure fluid flow path, and the second passage and the fourth passage are in fluid communication with each other and with the low-pressure fluid flow path;
a pressure sensor in fluid communication with the low-pressure fluid flow path; and
a console including a source of fluid refrigerant, wherein the console is in communication with the pressure sensor, and wherein the source of fluid refrigerant is in fluid communication with the high-pressure fluid flow path;
the console being coupled to the pressure sensor and terminating fluid flow in response to the pressure sensor indicating a fluid leak in the low-pressure fluid flow path.

10. The catheter system of claim 9, wherein the source of fluid refrigerant is pressurized, and the second fluid path is in communication with a vacuum source.

11. The catheter system of claim 9, further comprising a blood sensor in communication with one of the first and second fluid flow paths.

12. The catheter system of claim 9, further comprising a steering element at least partially disposed within the flexible catheter.

13. The catheter system of claim 12, further comprising a steering actuator coupled to the steering element.

14. A method of leak detection in a medical device, comprising:
coupling a first passage and a second passage defined by a first coupling body to a third passage and a fourth passage defined by a second coupling body, electrically connecting a first electrical connector of the first coupling body to a second electrical connector of the second coupling body, the coupling placing the first passage and third passage in fluid communication with a first fluid flow path of a flexible catheter, and the coupling placing the second passage and fourth passage in fluid communication with a second fluid flow path of a flexible catheter;
providing fluid refrigerant to the first fluid flow path at a predetermined operating pressure to cause fluid flow through the first fluid flow path;
detecting a change in operating pressure;
correlating the change in pressure to a leak indication; and
terminating fluid flow through the first fluid flow path if a leak is indicated.

15. A method of leak detection in a medical device, comprising:
coupling a first passage and a second passage defined by a first coupling body to a third passage and a fourth passage defined by a second coupling body, electrically connecting a first electrical connector of the first coupling body to a second electrical connector of the second coupling body, the coupling placing the first passage and third passage in fluid communication with a first fluid flow path of a flexible catheter, and the coupling placing the second passage and fourth passage being in fluid communication with a second fluid flow path of a flexible catheter;
providing fluid refrigerant to the first fluid flow path at a predetermined operating pressure to cause fluid flow through the first fluid flow path;
detecting blood in the flexible catheter;
correlating the blood to a leak indication; and
terminating fluid flow through the first fluid flow path if a leak is indicated.

* * * * *